United States Patent
Kimura et al.

(10) Patent No.: US 7,473,802 B2
(45) Date of Patent: Jan. 6, 2009

(54) METHOD OF PRODUCING NEAR-INFRARED ABSORBING DYE COMPOUND

(75) Inventors: Keizo Kimura, Odawara (JP); Tomohito Masaki, Odawara (JP); Osamu Uchida, Odawara (JP); Katsuyoshi Yamakawa, Odawara (JP)

(73) Assignee: FUJIFILM Corporation, Tokyo (JP)

( * ) Notice: Subject to any disclaimer, the term of this patent is extended or adjusted under 35 U.S.C. 154(b) by 230 days.

(21) Appl. No.: 11/514,181

(22) Filed: Sep. 1, 2006

(65) Prior Publication Data

US 2008/0221355 A1     Sep. 11, 2008

(30) Foreign Application Priority Data

Sep. 5, 2005     (JP)     ............... 2005-256834

(51) Int. Cl.
*C07C 55/06*     (2006.01)
*C07C 249/00*     (2006.01)

(52) U.S. Cl. ...................... 562/597; 564/269
(58) Field of Classification Search ............ None
See application file for complete search history.

(56) References Cited

U.S. PATENT DOCUMENTS 3,962,290 A     6/1976     Grosso

FOREIGN PATENT DOCUMENTS

| EP | 1564260 A1 | 8/2005 |
|---|---|---|
| EP | 1787978 A1 | 5/2007 |
| JP | 61-246391 A | 11/1986 |
| JP | 5-98243 A | 4/1993 |
| JP | 11-315054 A | 11/1999 |
| JP | 2003-055643 A * | 2/2003 |
| JP | 2003-55643 A | 2/2003 |

OTHER PUBLICATIONS

Zhifei Dai et al.; "Synthesis and Encapsulation of N,N,N',N'-Tetrakis[P-DI(n-Butyl)Aminophenyl]-p-Benzoquinone-bis(Imonium Hexafluoroantimonate)" Journal of Dispersion Science and Technology, vol. 23, No. 4, pp. 555-562, 2002.

* cited by examiner

*Primary Examiner*—Paul A. Zucker
(74) *Attorney, Agent, or Firm*—Birch, Stewart, Kolasch & Birch, LLP

(57) ABSTRACT

A method of producing a near-infrared absorbing dye compound, useful for image forming materials, infrared heat-sensitive recording devices, optical film materials, and the like, containing a process of reacting a compound represented by formula (I) with peroxomonosulfuric acid or its salt.

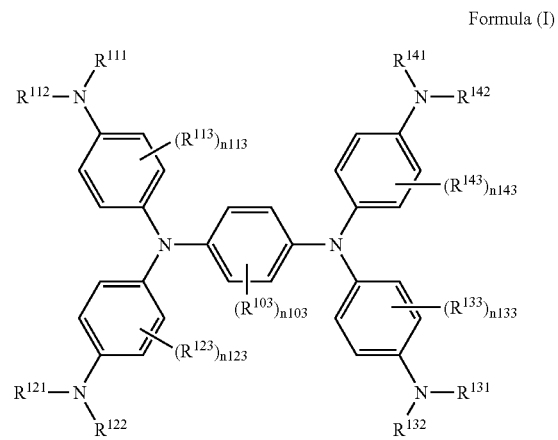

Formula (I)

wherein $R^{111}$, $R^{112}$, $R^{121}$, $R^{122}$, $R^{131}$, $R^{132}$, $R^{141}$ and $R^{142}$ each independently represent a hydrogen atom, an aliphatic group or an aromatic group; $R^{103}$, $R^{113}$, $R^{123}$, $R^{133}$ and $R^{143}$ each independently represent a substituent; and $n_{103}$, $n_{113}$, $n_{123}$, $n_{133}$ and $n_{143}$ each independently denote an integer from 0 to 4.

16 Claims, No Drawings

METHOD OF PRODUCING NEAR-INFRARED ABSORBING DYE COMPOUND

FIELD OF THE INVENTION

The present invention relates to a method of producing a near-infrared absorbing dye compound useful for image forming materials, infrared heat-sensitive recording materials, optical recording devices, optical film materials, and the like. Specifically, the present invention relates to a method in which an aminium salt and a diimmonium salt that are near-infrared absorption dye compounds, can be produced readily at low costs, and in a high yield.

BACKGROUND OF THE INVENTION

An aminium salt and a diimmonium salt are useful as near-infrared absorbing dyes that do not substantially absorb visible light but absorb infrared rays, and they have been studied enthusiastically (for example, JP-A-2003-280247 ("JP-A" means unexamined published Japanese patent application), JP-A-2003-295496, and JP-A-2004-145036).

As a method of producing an aminium salt or a diimmonium salt, methods in which an amino compound, that is a precursor, is oxidized by $Cu^{2+}$ (for example, JP-B-59-40825 ("JP-B" means examined Japanese patent publication) and JP-A-63-51462); by $Fe^{3+}$ (for example, JP-A-2-311447 and JP-A-11-315054); by utilizing an oxidizing reaction using a solid catalyst (for example, JP-A-5-98243); by a peroxodisulfate (for example, JP-A-2003-55643); by using silver hexafluoroantimonate (for example, Journal of Dispersion Science and Technology, vol. 23, p 555 (2002)), or by electrical oxidation (for example, JP-A-61-246391), have been known so far. All of these methods are unsatisfactory in a yield, and they have also a large environmental load because of the use of heavy metal ions. These methods also have such problems as high costs.

SUMMARY OF THE INVENTION

The present invention resides in a method of producing a near-infrared absorbing dye compound, comprising a process of reacting a compound represented by the following formula (I) with peroxomonosulfuric acid or its salt:

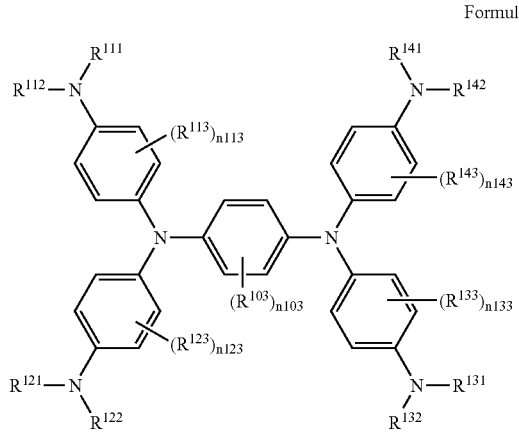

Formula (I)

wherein $R^{111}$, $R^{112}$, $R^{121}$, $R^{122}$, $R^{131}$, $R^{132}$, $R^{141}$ and $R^{142}$ each independently represent a hydrogen atom, an aliphatic group or an aromatic group; $R^{103}$, $R^{113}$, $R^{123}$, $R^{133}$ and $R^{143}$ each independently represent a substituent; and $n_{103}$, $n_{113}$, $n_{123}$, $n_{133}$ and $n_{143}$ each independently denote an integer from 0 to 4.

Other and further features and advantages of the invention will appear more fully from the following description.

DETAILED DESCRIPTION OF THE INVENTION

According to the present invention, there is provided the following means:

(1) A method of producing a near-infrared absorbing dye compound, comprising a process of reacting a compound represented by formula (I) with peroxomonosulfuric acid or its salt:

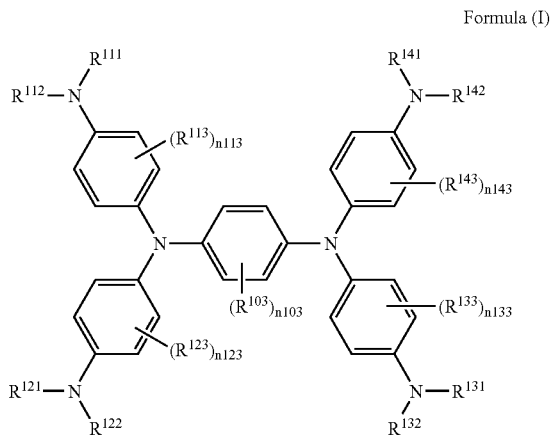

Formula (I)

wherein $R^{111}$, $R^{112}$, $R^{121}$, $R^{122}$, $R^{131}$, $R^{132}$, $R^{141}$ and $R^{142}$ each independently represent a hydrogen atom, an aliphatic group or an aromatic group; $R^{103}$, $R^{113}$, $R^{123}$, $R^{133}$ and $R^{143}$ each independently represent a substituent; and $n_{103}$, $n_{113}$, $n_{123}$, $n_{133}$ and $n_{143}$ each independently denote an integer from 0 to 4.

(2) A production method according to the above (1), wherein the salt of peroxomonosulfuric acid is potassium peroxohydrogen monosulfate.

(3) A production method according to the above (1) or (2), wherein the near-infrared absorbing dye compound is a diimmonium salt represented by formula (II):

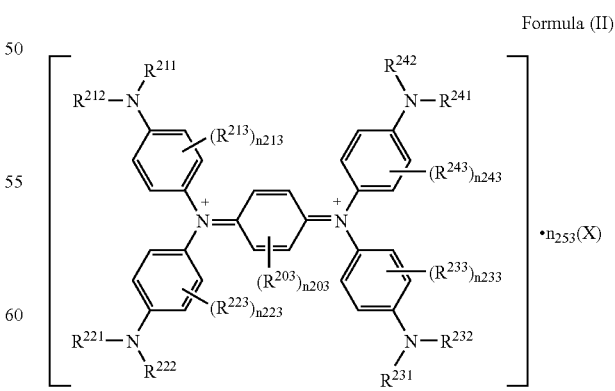

Formula (II)

wherein $R^{211}$, $R^{212}$, $R^{221}$, $R^{222}$, $R^{231}$, $R^{232}$, $R^{241}$ and $R^{242}$ each independently represent a hydrogen atom, an aliphatic group or an aromatic group; $R^{203}$, $R^{213}$, $R^{223}$, $R^{233}$ and $R^{243}$ each independently represent a substituent; $n_{203}$, $n_{213}$, $n_{223}$, $n_{233}$ and $n_{243}$ each independently denote an integer from 0 to 4; X represents a monovalent or divalent anion; and $n_{253}$ represents a number of 1 or 2, provided that the product of the valence number of X and $n_{253}$ is 2.
(4) The production method according to the above (3), wherein X is a divalent anion.
(5) A production method according to any one of the above (1) to (4), wherein an acid or its salt coexists in the above process.
(6) A production method according to the above (5), wherein the above acid or salt is a perchloric acid or a perchlorate.

Embodiments of the present invention will be explained hereinbelow.

In this specification, first, the aliphatic group means alkyl groups, substituted alkyl groups, alkenyl groups, substituted alkenyl groups, alkynyl groups, substituted alkynyl groups, aralkyl groups and substituted aralkyl groups. The alkyl groups may be branched or may form a ring (specifically, a cycloalkyl group). The number of carbon atoms of the alkyl group is preferably 1 to 20 and more preferably 1 to 18. The alkyl part of the substituted alkyl group is the same as the above alkyl group. The alkenyl part of the substituted alkenyl group is the same as the above alkenyl group. The alkenyl group may be branched or may form a ring (specifically, a cycloalkenyl group). The number of carbon atoms of the alkenyl group is preferably 2 to 20 and more preferably 2 to 18. The alkenyl part of the substituted alkenyl group is the same as the above alkenyl group. The alkynyl group may be branched or may form a ring (specifically, a cycloalkynyl group). The number of carbon atoms of the alkynyl group is preferably 2 to 20 and more preferably 2 to 18. The alkynyl part of the substituted alkynyl group is the same as the above alkynyl group. The alkyl group of the aralkyl group and substituted aralkyl group is the same as the above alkyl group. The aryl part of the aralkyl group and the substituted aralkyl group is the same as the following aryl group.

Examples of the substituent in the alkyl portion of the substituted alkyl group, substituted alkenyl groups, substituted alkynyl groups and substituted aralkyl groups include a halogen atom (e.g., chlorine, bromine, iodine atom), an alkyl group [which means a linear, branched or cyclic substituted or unsubstituted alkyl group and which includes an alkyl group (preferably an alkyl group having from 1 to 30 carbon atoms, e.g., methyl, ethyl, n-propyl, isopropyl, tert-butyl, n-octyl, eicosyl, 2-chloroethyl, 2-cyanoethyl, 2-ethylhexyl), a cycloalkyl group (preferably a substituted or unsubstituted cycloalkyl group having from 3 to 30 carbon atoms, e.g., cyclohexyl, cyclopentyl, 4-n-dodecyl-cyclohexyl), a bicycloalkyl group (preferably a substituted or unsubstituted bicycloalkyl group having from 5 to 30 carbon atoms, namely, a monovalent group resultant from removing one hydrogen atom of a bicycloalkane having from 5 to 30 carbon atoms, e.g., bicyclo[1,2,2]heptan-2-yl, bicyclo[2,2,2]octan-3-yl), and a group having many cyclic structures, such as tricyclo-structure; the alkyl group in the substituents described below (for example, an alkyl group in an alkylthio group) means an alkyl group having such a concept], an alkenyl group [which means a linear, branched or cyclic substituted or unsubstituted alkenyl group and which includes an alkenyl group (preferably a substituted or unsubstituted alkenyl group having from 2 to 30 carbon atoms, e.g., vinyl, allyl, prenyl, geranyl, oreyl), a cycloalkenyl group (preferably a substituted or unsubstituted cycloalkenyl group having from 3 to 30 carbon atoms, namely, a monovalent group resultant from removing one hydrogen atom of a cycloalkene having from 3 to 30 carbon atoms, e.g., 2-cyclopenten-1-yl, 2-cyclohexen-1-yl), and a bicycloalkenyl group (a substituted or unsubstituted bicycloalkenyl group, preferably a substituted or unsubstituted bicycloalkenyl group having from 5 to 30 carbon atoms, namely, a monovalent group resultant from removing one hydrogen atom of a bicycloalkene having one double bond, e.g., bicyclo[2,2,1]hept-2-en-1-yl, bicyclo[2,2,2]oct-2-en-4-yl)], an alkynyl group (preferably a substituted or unsubstituted alkynyl group having from 2 to 30 carbon atoms, e.g., ethynyl, propargyl, trimethylsilylethynyl), an aryl group (preferably a substituted or unsubstituted aryl group having from 6 to 30 carbon atoms, e.g., phenyl, p-tolyl, naphthyl, m-chlorophenyl, o-hexadecanoylaminophenyl), a heterocyclic group (preferably a monovalent group resultant from removing one hydrogen atom of a 5- or 6-membered substituted or unsubstituted aromatic or non-aromatic heterocyclic compound, more preferably a 5- or 6-membered aromatic heterocyclic group having from 3 to 30 carbon atoms, e.g., 2-furyl, 2-thienyl, 2-pyrimidinyl, 2-benzothiazolyl), a cyano group, a hydroxyl group, a nitro group, a carboxyl group, an alkoxy group (preferably a substituted or unsubstituted alkoxy group having from 1 to 30 carbon atoms, e.g., methoxy, ethoxy, isopropoxy, tert-butoxy, n-octyloxy, 2-methoxyethoxy), an aryloxy group (preferably a substituted or unsubstituted aryloxy group having from 6 to 30 carbon atoms, e.g., phenoxy, 2-methylphenoxy, 4-tert-butylphenoxy, 3-nitrophenoxy, 2-tetradecanoylaminophenoxy), a silyloxy group (preferably a silyloxy group having from 3 to 20 carbon atoms, e.g., trimethylsilyloxy, tert-butyldimethylsilyloxy), a heterocyclic oxy group (preferably a substituted or unsubstituted heterocyclic oxy group having from 2 to 30 carbon atoms, e.g., 1-phenyltetrazol-5-oxy, 2-tetrahydropyranyloxy), an acyloxy group (preferably a formyloxy group, a substituted or unsubstituted alkylcarbonyloxy group having from 2 to 30 carbon atoms or a substituted or unsubstituted arylcarbonyloxy group having from 6 to 30 carbon atoms, e.g., formyloxy, acetyloxy, pivaloyloxy, stearoyloxy, benzoyloxy, p-methoxyphenylcarbonyloxy), a carbamoyloxy group (preferably a substituted or unsubstituted carbamoyloxy group having from 1 to 30 carbon atoms, e.g., N,N-dimethylcarbamoyloxy, N,N-diethylcarbamoyloxy, morpholinocarbonyloxy, N,N-di-n-octylaminocarbonyloxy, N-n-octylcarbamoyloxy), an alkoxycarbonyloxy group (preferably a substituted or unsubstituted alkoxycarbonyloxy group having from 2 to 30 carbon atoms, e.g., methoxycarbonyloxy, ethoxycarbonyloxy, tert-butoxycarbonyloxy, n-octyloxycarbonyloxy), an aryloxycarbonyloxy group (preferably a substituted or unsubstituted aryloxycarbonyloxy group having from 7 to 30 carbon atoms, e.g., phenoxycarbonyloxy, p-methoxyphenoxycarbonyloxy, p-n-hexadecyloxyphenoxycarbonyloxy), an amino group (preferably an amino group, a substituted or unsubstituted alkylamino group having from 1 to 30 carbon atoms or a substituted or unsubstituted anilino group having from 6 to 30 carbon atoms, e.g., amino, methylamino, dimethylamino, anilino, N-methylanilino, diphenylamino), an acylamino group (preferably a formylamino group, a substituted or unsubstituted alkylcarbonylamino group having from 1 to 30 carbon atoms or a substituted or unsubstituted arylcarbonylamino group having from 6 to 30 carbon atoms, e.g., formylamino, acetylamino, pivaloylamino, lauroylamino, benzoylamino, 3,4,5-tri-n-octyloxyphenylcarbonylamino), an aminocarbonylamino group (preferably a substituted or unsubstituted aminocarbonylamino group having from 1 to 30 carbon atoms, e.g., carbamoylamino, N,N-dimethylaminocarbonylamino, N,N-diethylaminocarbonylamino, morpholinocarbonylamino), an alkoxycarbonylamino group (preferably a substituted or unsubstituted alkoxycarbonylamino group having from 2 to 30 carbon atoms, e.g., methoxycarbonylamino, ethoxycarbonylamino, tert-butoxycarbonylamino, n-octadecyloxycarbonylamino, N-methyl-methoxycarbonylamino), an aryloxycarbonylamino group (preferably a substituted or unsubstituted aryloxycarbonylamino group having from 7 to 30 carbon atoms, e.g., phenoxycarbonylamino, p-chlorophenoxycarbonylamino, m-(n-octyloxy)phenoxycarbonylamino), a sulfamoylamino group (preferably a substituted or unsubstituted sulfamoylamino group having from 0 to 30 carbon atoms, e.g., sulfamoylamino, N,N-dimethylaminosulfonylamino, N-n-octylaminosulfonylamino), an alkyl- or aryl-sulfonylamino group (preferably a substituted or unsubstituted alkylsulfonylamino group having from 1 to 30 carbon atoms or a substituted or unsubstituted arylsulfonylamino group having from 6 to 30 carbon atoms, e.g., methylsulfonylamino, butylsulfonylamino, phenylsulfonylamino, 2,3,5-trichlorophenylsulfonylamino, p-methylphenylsulfonylamino), a mercapto group, an alkylthio group (preferably a substituted or unsubstituted alkylthio group having from 1 to 30 carbon atoms, e.g., methylthio, ethylthio, n-hexadecylthio), an arylthio group (preferably a substituted or unsubstituted arylthio group having from 6 to 30 carbon atoms, e.g., phenylthio, p-chlorophenylthio, m-methoxyphenylthio), a heterocyclic thio group (preferably a substituted or unsubstituted heterocyclic thio group having from 2 to 30 carbon atoms, e.g., 2-benzothiazolylthio, 1-phenyltetrazol-5-ylthio), a sulfamoyl group (preferably a substituted or unsubstituted sulfamoyl group having from 0 to 30 carbon atoms, e.g., N-ethylsulfamoyl, N-(3-dodecyloxypropyl)sulfamoyl, N,N-dimethylsulfamoyl, N-acetylsulfamoyl, N-benzoylsulfamoyl, N—(N'-phenylcarbamoyl)sulfamoyl), a sulfo group, an alkyl- or aryl-sulfinyl group (preferably a substituted or unsubstituted alkylsulfinyl group having from 1 to 30 carbon atoms or a substituted or unsubstituted arylsulfinyl group having from 6 to 30 carbon atoms, e.g., methylsulfinyl, ethylsulfinyl, phenylsulfinyl, p-methylphenylsulfinyl), an alkyl- or aryl-sulfonyl group (preferably a substituted or unsubstituted alkylsulfonyl group having from 1 to 30 carbon atoms or a substituted or unsubstituted arylsulfonyl group having from 6 to 30 carbon atoms, e.g., methylsulfonyl, ethylsulfonyl, phenylsulfonyl, p-methylphenylsulfonyl), an acyl group (preferably a formyl group, a substituted or unsubstituted alkylcarbonyl group having from 2 to 30 carbon atoms, a substituted or unsubstituted arylcarbonyl group having from 7 to 30 carbon atoms or a substituted or unsubstituted heterocyclic carbonyl group having from 4 to 30 carbon atoms and being bonded to a carbonyl group through a carbon atom, e.g., acetyl, pivaloyl, 2-chloroacetyl, stearoyl, benzoyl, p-n-octyloxyphenylcarbonyl, 2-pyridylcarbonyl, 2-furylcarbonyl), an aryloxycarbonyl group (preferably a substituted or unsubstituted aryloxycarbonyl group having from 7 to 30 carbon atoms, e.g., phenoxycarbonyl, o-chlorophenoxycarbonyl, m-nitrophenoxycarbonyl, p-tert-butylphenoxycarbonyl), an alkoxycarbonyl group (preferably a substituted or unsubstituted alkoxycarbonyl group having from 2 to 30 carbon atoms, e.g., methoxycarbonyl, ethoxycarbonyl, tert-butoxycarbonyl, n-octadecyloxycarbonyl), a carbamoyl group (preferably a substituted or unsubstituted carbamoyl group having from 1 to 30 carbon atoms, e.g., carbamoyl, N-methylcarbamoyl, N,N-dimethylcarbamoyl, N,N-di-n-octylcarbamoyl, N-(methylsulfonyl)-carbamoyl), an aryl- or heterocyclic-azo group (preferably a substituted or unsubstituted arylazo group having from 6 to 30 carbon atoms or a substituted or unsubstituted heterocyclic-azo group having from 3 to 30 carbon atoms, e.g., phenylazo, p-chlorophenylazo, 5-ethylthio-1,3,4-thiadiazol-2-ylazo), an imido group (preferably N-succinimido, N-phthalimido), a phosphino group (preferably a substituted or unsubstituted phosphino group having from 2 to 30 carbon atoms, e.g., dimethylphosphino, diphenylphosphino, methylphenoxyphosphino), a phosphinyl group (preferably a substituted or unsubstituted phosphinyl group having from 2 to 30 carbon atoms, e.g., phosphinyl, dioctyloxyphosphinyl, diethoxyphosphinyl), a phosphinyloxy group (preferably a substituted or unsubstituted phosphinyloxy group having from 2 to 30 carbon atoms, e.g., diphenoxyphosphinyloxy, dioctyloxyphosphinyloxy), a phosphinylamino group (preferably a substituted or unsubstituted phosphinylamino group having from 2 to 30 carbon atoms, e.g., dimethoxyphosphinylamino, dimethylaminophosphinylamino), or a silyl group (preferably a substituted or unsubstituted silyl group having from 3 to 30 carbon atoms, e.g., trimethylsilyl, tert-butyldimethylsilyl, phenyldimethylsilyl).

Among the above functional groups, those having a hydrogen atom may be further substituted with the above group at the position from which the hydrogen atom is removed. Examples of such a functional group include an alkylcarbonylaminosulfonyl group, arylcarbonylaminosulfonyl group, alkylsulfonylaminocarbonyl group and arylsulfonylaminocarbonyl group. Specific examples of these groups include methylsulfonylaminocarbonyl, p-methylphenylsulfonylaminocarbonyl, acetylaminosulfonyl and benzoylaminosulfonyl.

Examples of the substituent of the aryl part of the substituted aralkyl group include substituents of the following substituted aryl group.

The aromatic group in this specification means an aryl group and a substituted aryl group. Also, these aromatic groups may be condensed with aliphatic rings, other aromatic rings or hetero rings. The number of carbon atoms of the aromatic group is preferably 6 to 40, more preferably 6 to 30 and still more preferably 6 to 20. Among these groups, the aryl group is preferably phenyl or naphthyl and particularly preferably phenyl.

The aryl part of the substituted aryl group is the same as the above aryl group. Examples of the substituent of the substituted aryl group include those given as the substituents of the alkyl parts of the previous substituted alkyl group, substituted alkenyl group, substituted alkynyl group and substituted aralkyl group.

Next, the compounds represented by the formulae (I) and (II) will be explained.

In the formula (I), $R^{111}$, $R^{112}$, $R^{121}$, $R^{122}$, $R^{131}$, $R^{132}$, $R^{141}$ and $R^{142}$ are respectively preferably a hydrogen atom, an alkyl group, an alkenyl group, an alkynyl group or an aryl group, more preferably a hydrogen atom, an alkyl group having 1 to 20 carbon atoms, an alkenyl group having 2 to 20 carbon atoms, an alkynyl group having 2 to 20 carbon atoms or an aryl group having 6 to 20 carbon atoms, still more preferably an alkyl group having 1 to 10 carbon atoms, an alkenyl group having 2 to 10 carbon atoms or an aryl group having 6 to 10 carbon atoms, even more preferably an alkyl group having 1 to 8 carbon atoms or an aryl group having 6 to 8 carbon atoms and most preferably an alkyl group having 2 to 6 carbon atoms. Also, all of $R^{111}$, $R^{112}$, $R^{121}$, $R^{122}$, $R^{131}$, $R^{132}$, $R^{141}$ and $R^{142}$ are preferably the same.

$R^{103}$, $R^{113}$, $R^{123}$, $R^{133}$ and $R^{143}$ are preferably a halogen atom, an alkyl group, an alkenyl group, an alkynyl group, an aryl group, a cyano group, a hydroxyl group, a carboxyl group, an alkoxy group, an aryloxy group, a silyloxy group, an acyloxy group, a carbamoyloxy group, an alkoxycarbonyloxy group, an aryloxycarbonyloxy group, an amino group, an acylamino group, an aminocarbonylamino group, an alkoxycarbonylamino group, an aryloxycarbonylamino group, a sulfamoylamino group, an alkyl or arylsulfonylamino group, a mercapto group, an alkylthio group, an arylthio group, a sulfamoyl group, a sulfo group, an alkyl or arylsulfinyl group, an alkyl or arylsulfonyl group, an acyl group, an aryloxycarbonyl group, an alkoxycarbonyl group, a carbamoyl group, an imido group, a phosphino group, a phosphinyl group, a phosphinyloxy group, a phosphinylamino group or a silyl group, more preferably a halogen atom, an alkyl group, an alkenyl group, an aryl group, a cyano group, a hydroxyl group, a carboxyl group, an alkoxy group, an aryloxy group, a silyloxy group, an amino group, an alkylthio group, an arylthio group, an imido group or a silyl group, still more preferably a halogen atom, an alkyl group, an aryl group, an alkoxy group, an aryloxy group, a silyloxy group and an amino group or most preferably an alkyl group. Also, all of $R^{113}$, $R^{123}$, $R^{133}$ and $R^{1143}$ are preferably the same.

$n_{103}$, $n_{113}$, $n_{123}$, $n_{133}$ and $n_{143}$ are preferably 0 to 3, more preferably 0 to 2, still more preferably 0 or 1 and most preferably 0.

In the formula (II), $R^{211}$, $R^{212}$, $R^{221}$, $R^{222}$, $R^{231}$, $R^{232}$, $R^{241}$ and $R^{242}$ respectively have the same meaning as above $R^{111}$ and the preferable range is also the same. Also, all of $R^{211}$, $R^{212}$, $R^{221}$, $R^{222}$, $R^{231}$, $R^{232}$, $R^{241}$ and $R^{242}$ are preferably the same.

$R^{203}$, $R^{213}$, $R^{223}$, $R^{233}$ and $R^{243}$ respectively have the same meaning as above $R^{103}$ and the preferable range is also the same. Also, all of $R^{213}$, $R^{223}$, $R^{233}$ and $R^{243}$ are preferably the same.

$n_{203}$, $n_{213}$, $n_{223}$, $n_{233}$ and $n_{243}$ respectively have the same meaning as above $n_{103}$ and the preferable range is also the same.

X represents a monovalent or divalent anion. As is the case that X is monovalent anion, X is preferably a perchloric acid ion, a carboxylic acid ion, a sulfonic acid ion, a hexafluorophosphoric acid ion, a tetrafluoroboric acid ion or a hexafluoroantimonic acid ion, more preferably a perchloric acid ion, a sulfonic acid ion, a hexafluorophosphoric acid ion, a tetrafluoroboric acid ion or a hexafluoroantimonic acid ion, still more preferably a perchloric acid ion, a hexafluorophosphoric acid ion, a tetrafluoroboric acid ion or a hexafluoroantimonic acid ion, and most preferably a perchloric acid ion. On the other hand as is the case that X is divalent anion, X is preferably carbonate ion, sulfate ion, oxalate ion, succinate ion, malonate ion, chromate ion, bichromate ion, and teteraborate ion, more preferably carbonate ion, sulfate ion, oxalate ion, and teteraborate ion, and further preferably carbonate ion and sulfate ion, and still further preferably sulfate ion.

n253 represents a number of 1 or 2, provided that the product of the valence number of X and n253 is 2.

Specific examples of the compounds represented by the formulae (I) and (II) will be shown below: however, these examples are not intended to be limiting of the present invention.

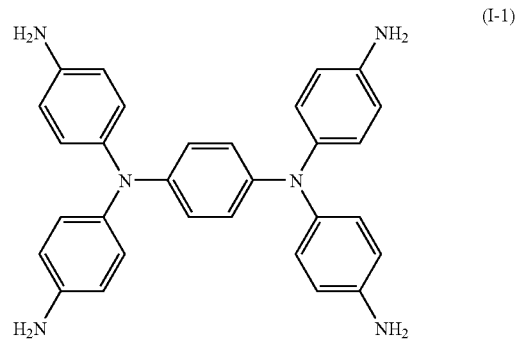

(I-1)

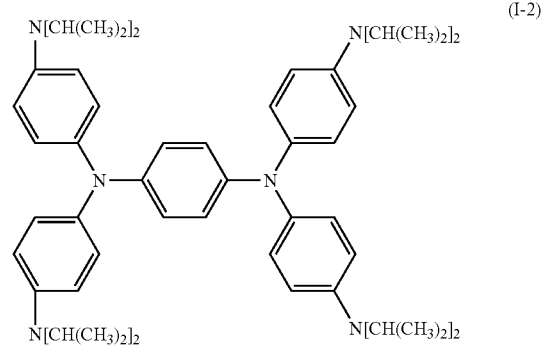

(I-2)

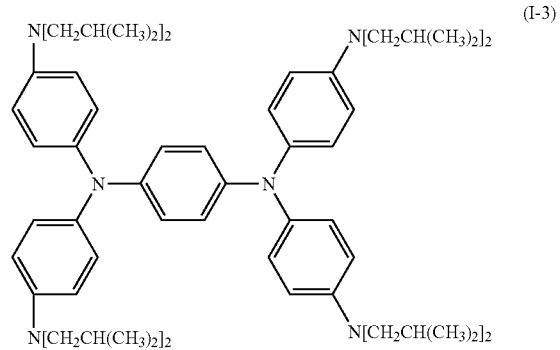

(I-3)

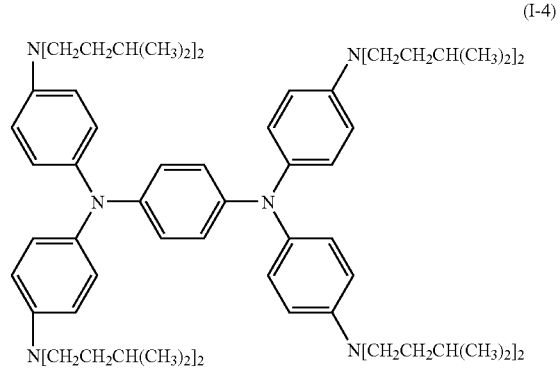

(I-4)

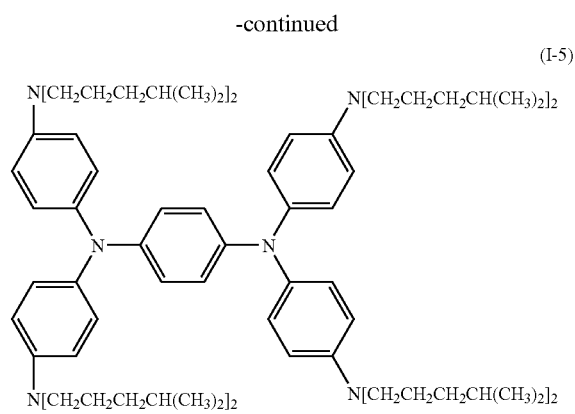
(I-5)
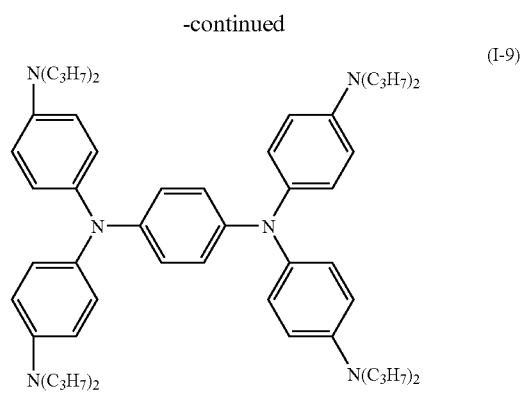
(I-9)
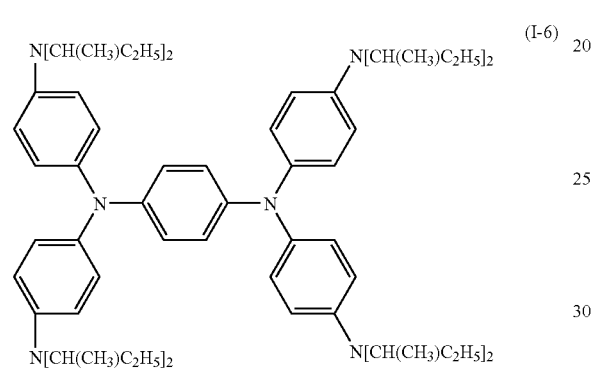
(I-6)
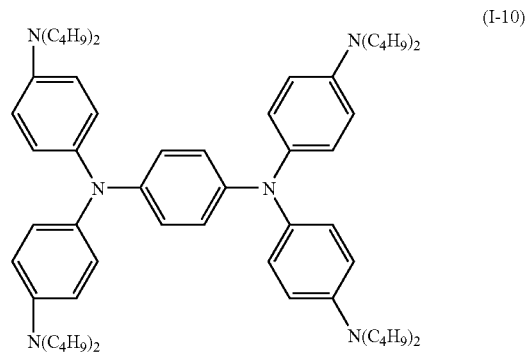
(I-10)
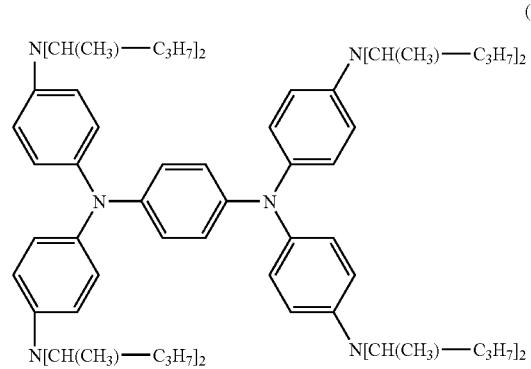
(I-7)
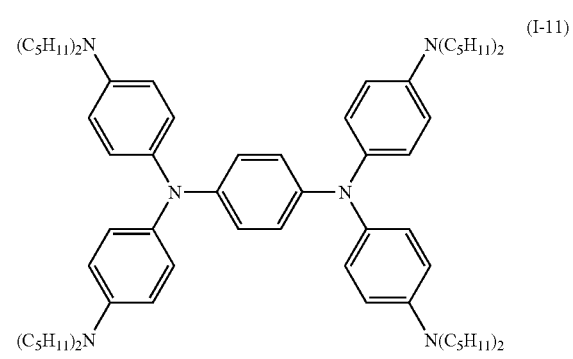
(I-11)
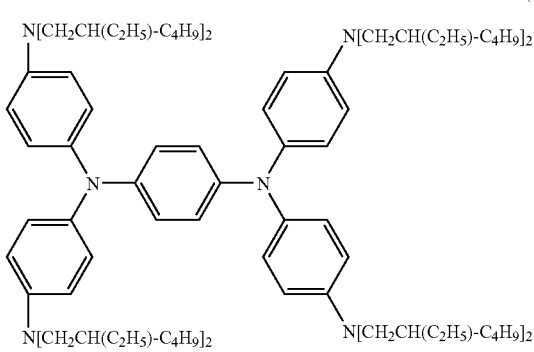
(I-8)
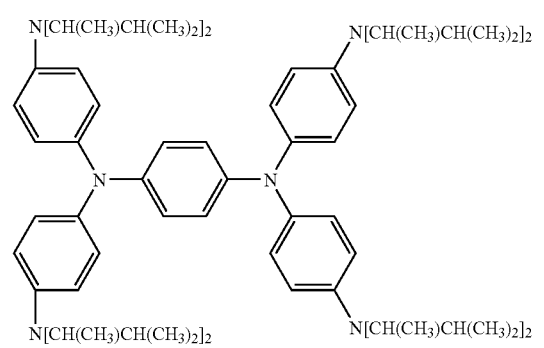
(I-12)

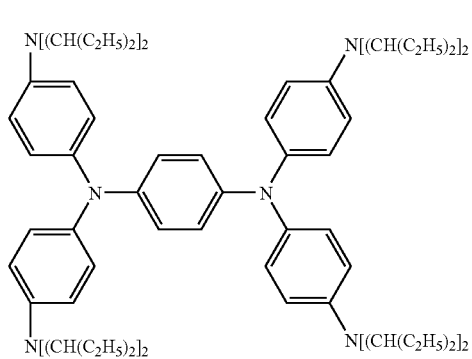
(I-13)
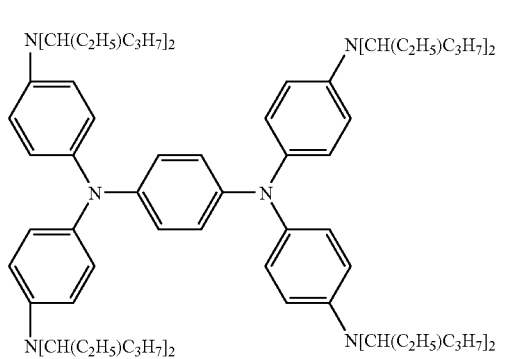
(I-17)
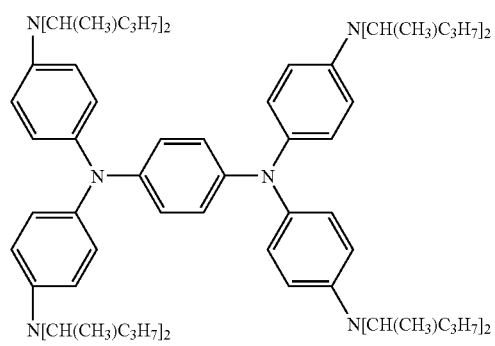
(I-14)
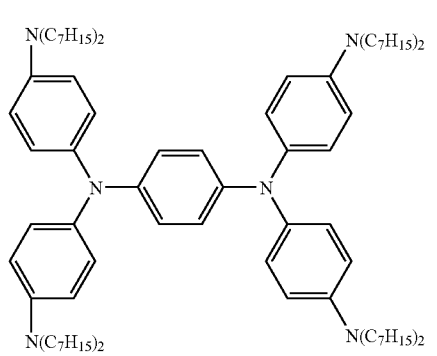
(I-18)
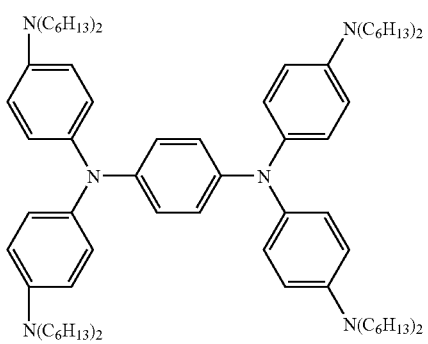
(I-15)
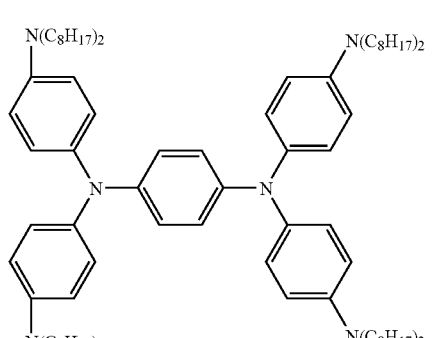
(I-19)
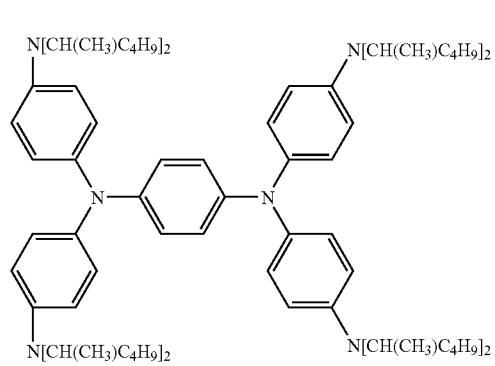
(I-16)
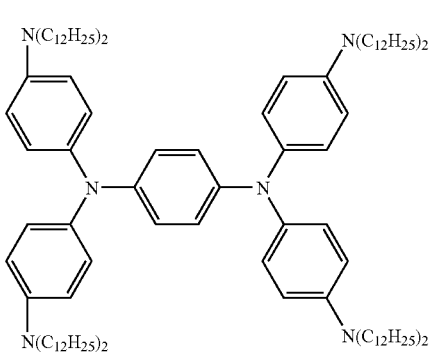
(I-20)

-continued
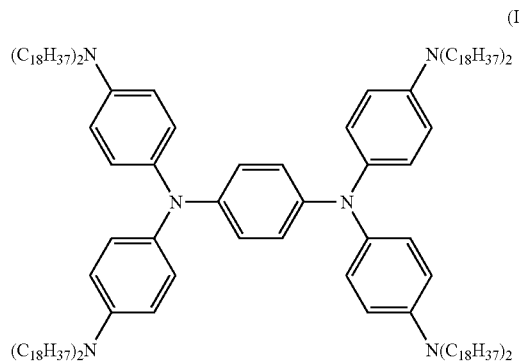
(I-21)
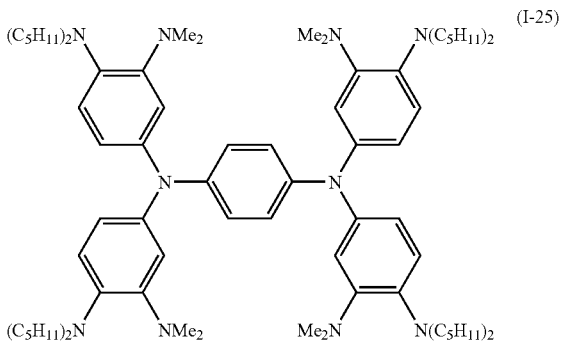
(I-25)
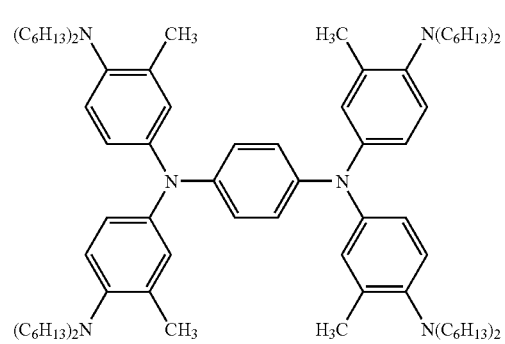
(I-22)
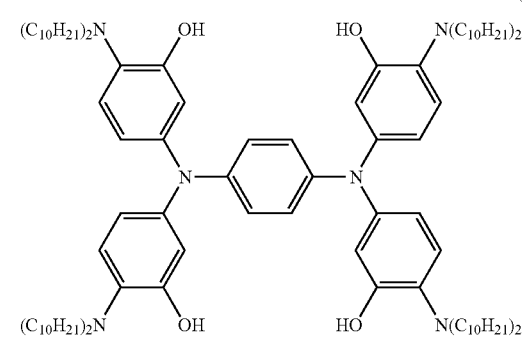
(I-26)
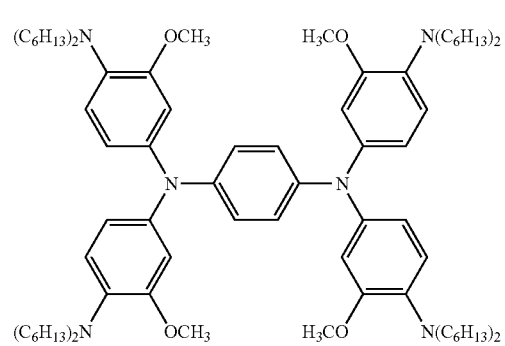
(I-23)
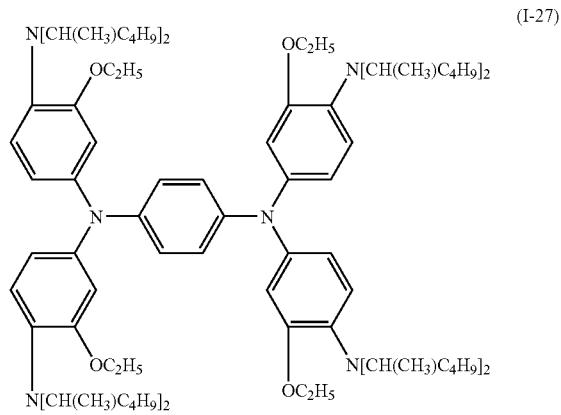
(I-27)
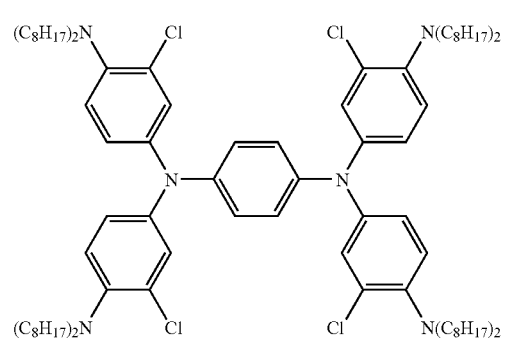
(I-24)
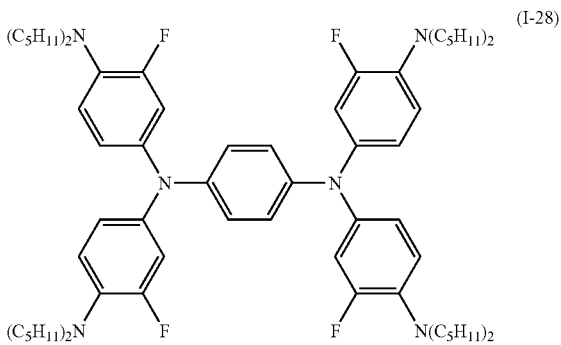
(I-28)

-continued
(I-29)
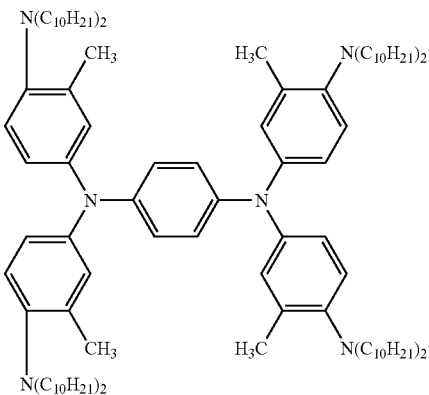
(I-30)
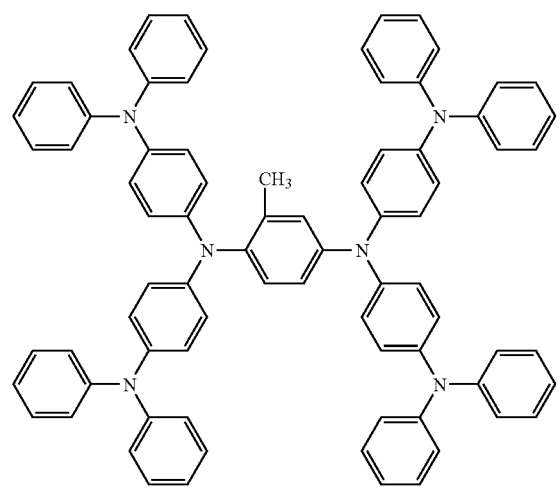
(II-1)
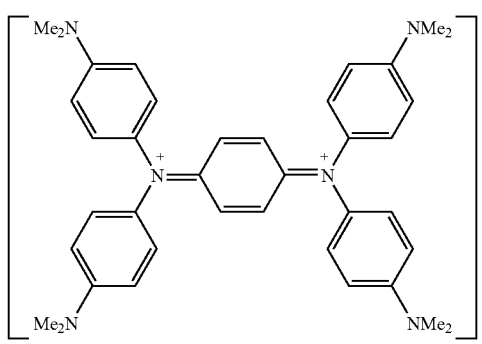
(II-2)
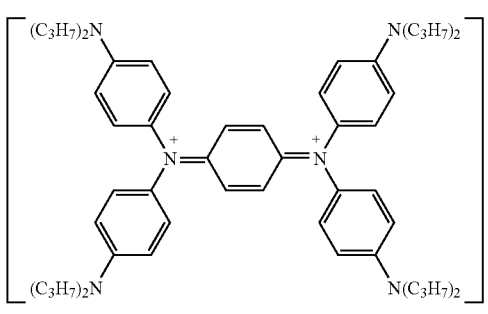
-continued
(II-3)
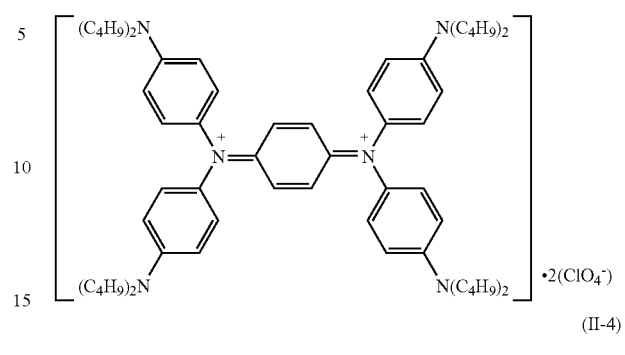
(II-4)
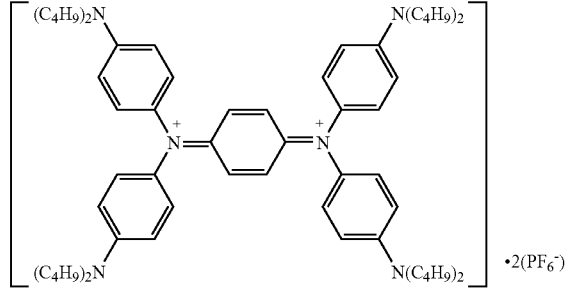
(II-5)
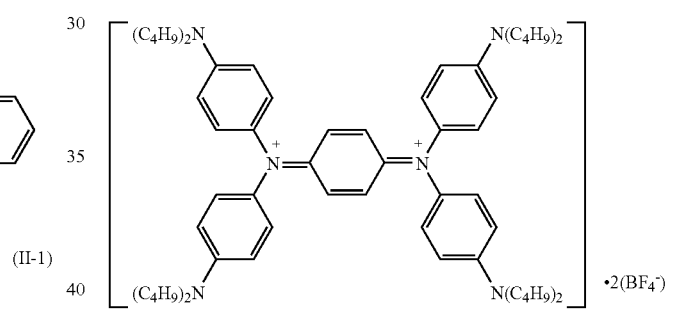
(II-6)
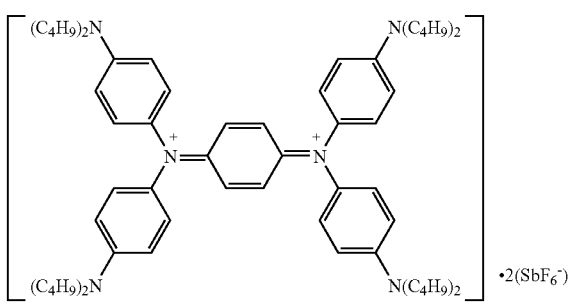
(II-7)
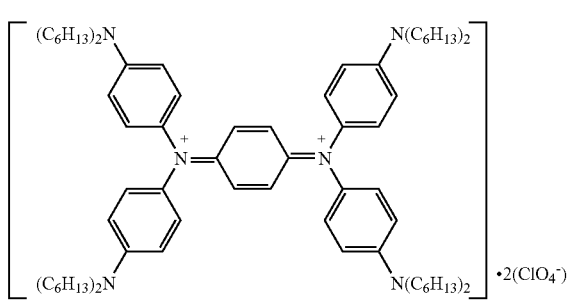

-continued
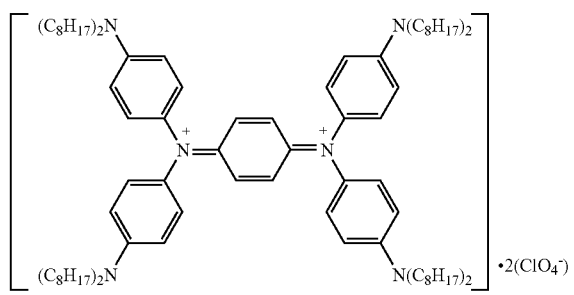
(II-8)
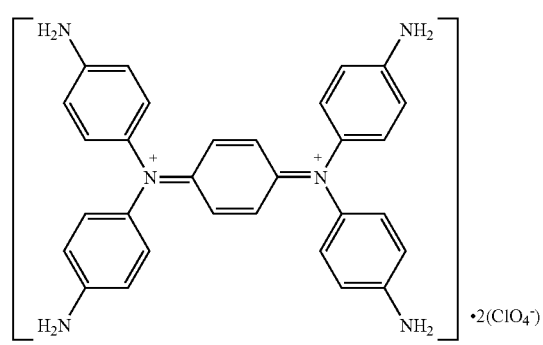
(II-9)
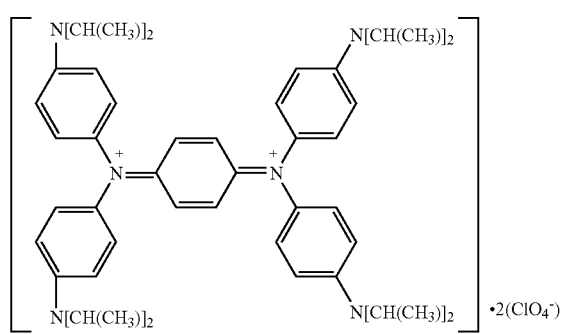
(II-10)
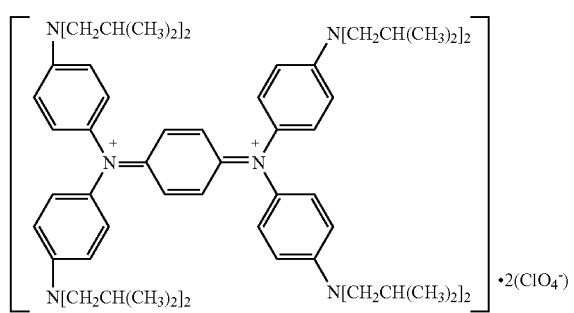
(II-11)
-continued
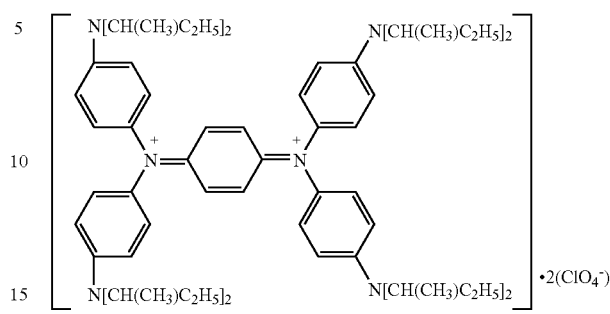
(II-12)
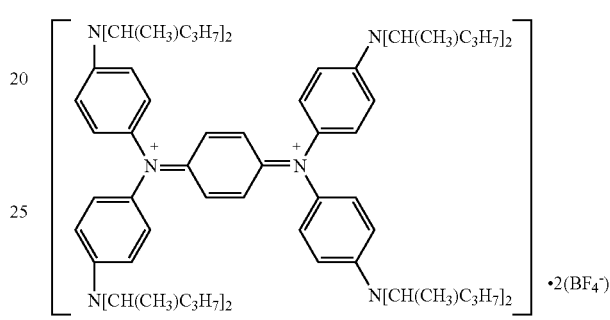
(II-13)
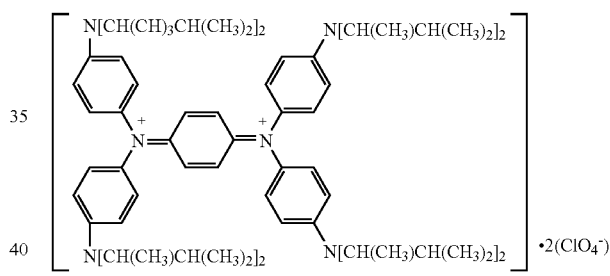
(II-14)
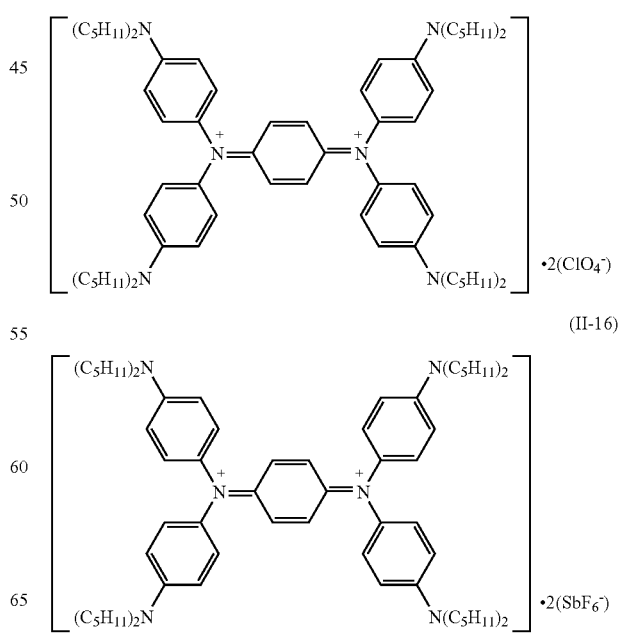
(II-15)
(II-16)

-continued
(II-17)
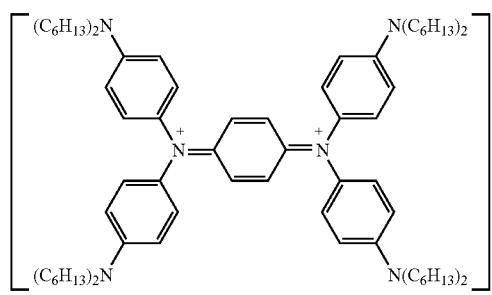
(II-18)
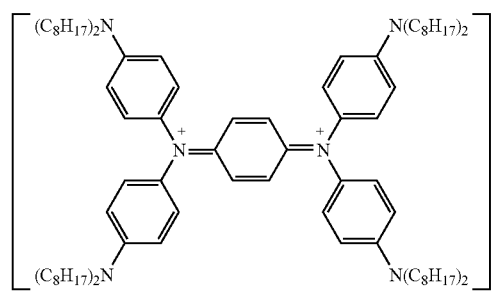
(II-19)
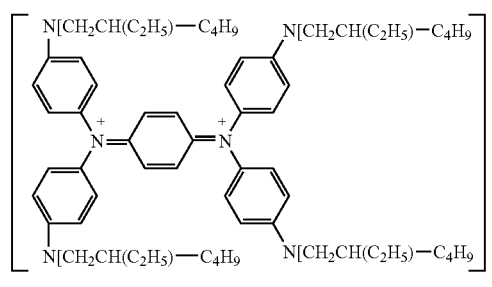
(II-20)
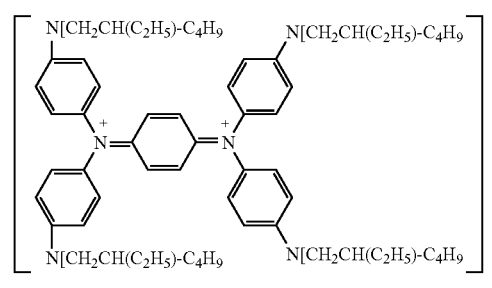
(II-21)
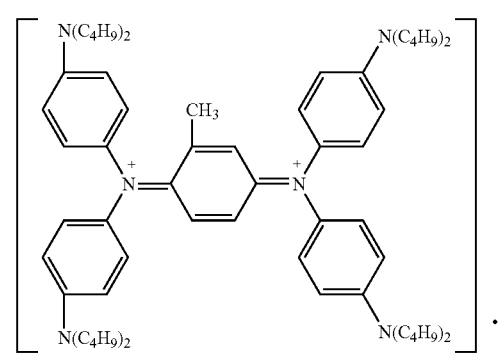
(II-22)
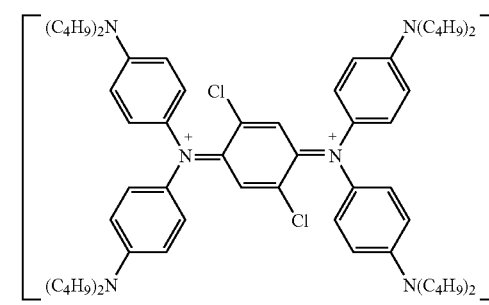
(II-23)
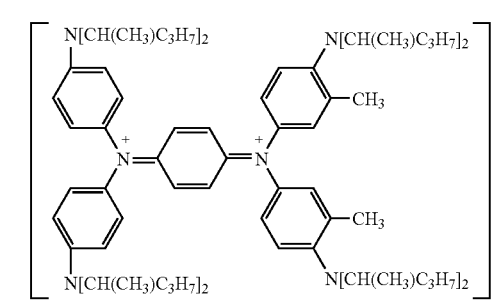
(II-24)
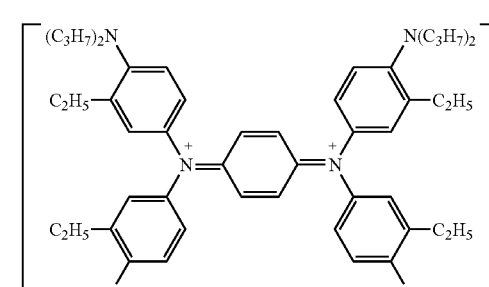
(II-25)
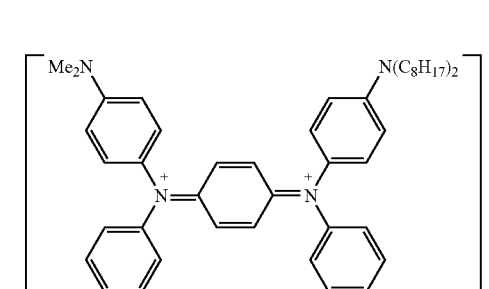
(II-26)
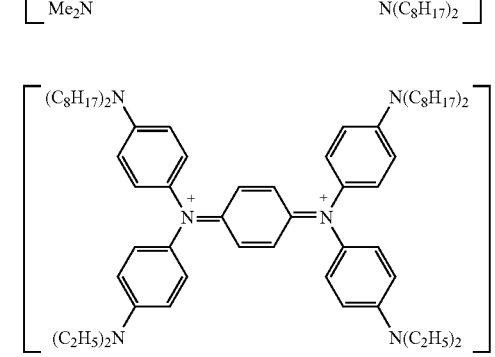

-continued

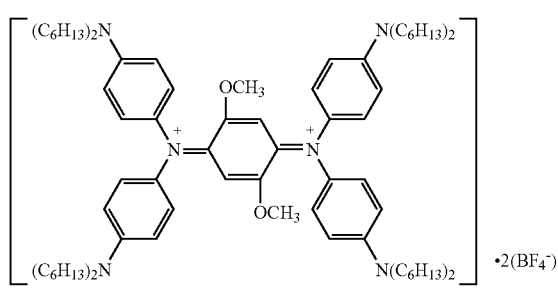 (II-27)

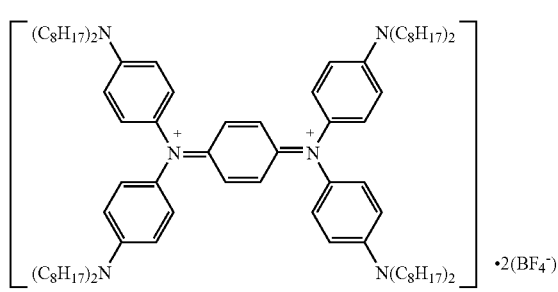 (II-28)

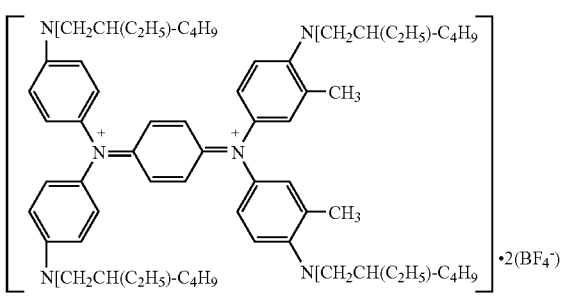 (II-29)

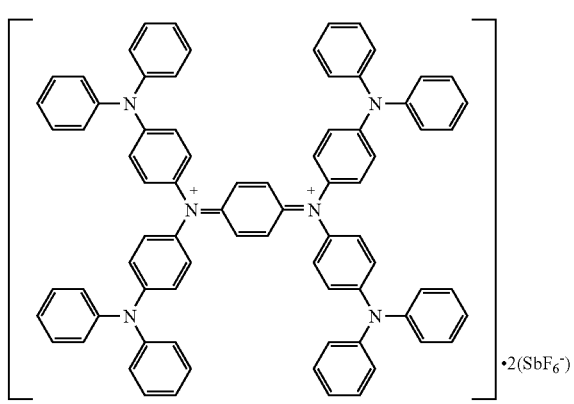 (II-30)

-continued

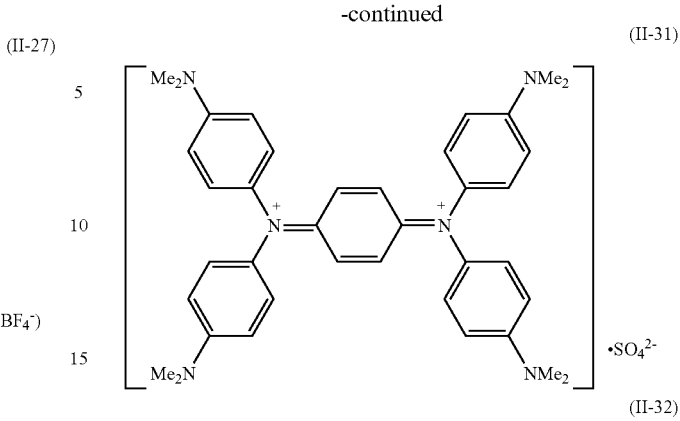 (II-31)

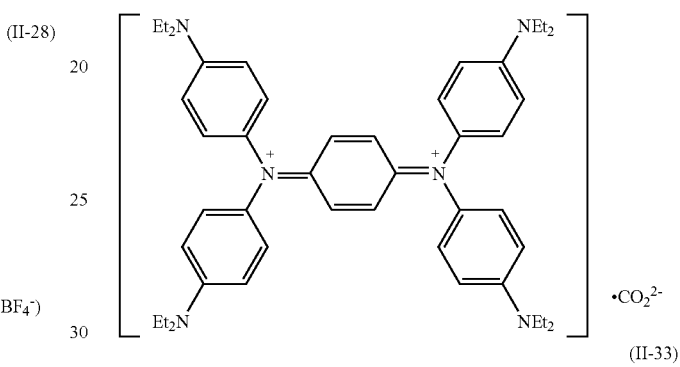 (II-32)

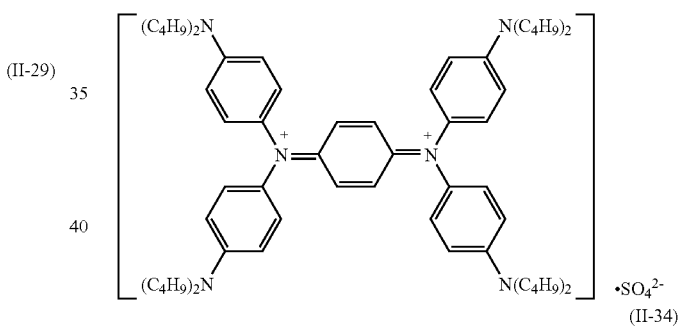 (II-33)

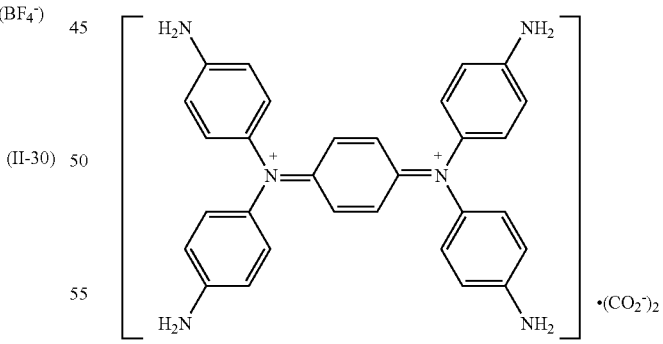 (II-34)

The peroxomonosulfuric acid (molecular formula: $H_2SO_5$) or its salt to be used in the present invention is preferably peroxomonosulfuric acid, sodium peroxomonosulfate, sodium peroxohydrogen monosulfate, potassium peroxomonosulfate, potassium peroxohydrogen monosulfate, magnesium peroxomonosulfate, calcium peroxomonosulfate and ammonium peroxomonosulfate, more preferably sodium peroxomonosulfate, sodium peroxohydrogen monosulfate, potassium peroxomonosulfate, potassium peroxohydrogen monosulfate and ammonium peroxomonosulfate, still more preferably sodium peroxomonosulfate, sodium peroxohydrogen monosulfate, potassium peroxomonosulfate and potassium peroxohydrogen monosulfate, and most preferably potassium peroxohydrogen monosulfate (molecular formula: $KHSO_5$). Also, this may be those forming compositions mixed with sulfates. Examples of the compositions mixed with sulfates include $2KHSO_5 \cdot KHSO_4 \cdot K_2SO_4$, examples of which include OXONE (trade name) manufactured by Du Pont.

It is preferable that an acid or its salt coexist in the oxidizing process of the present invention.

Examples of such an acid (protonic body) or its salt include acids such as perchloric acid, benzoic acid, hexafluorophosphoric acid, tetrafluoroboric acid, p-toluenesulfonic acid, methanesulfonic acid, ethanesulfonic acid, benzenesulfonic acid, naphthalene-1,5-disulfonic acid, trifluoroacetic acid, hexafluoroantimonic acid, trifluoromethanesulfonic acid and molybudenic acid or its ammonium salts, lithium salts, sodium salts, potassium salts and magnesium salts of these acids. Among these compounds, protonic bodies of a perchloric acid, hexafluorophosphoric acid, tetrafluoroboric acid, methanesulfonic acid, hexafluoroantimonic acid or trifluoromethanesulfonic acid, ammonium salts, sodium salts or potassium salts of these protonic bodies, more preferably protonic bodies of a perchloric acid, hexafluorophosphoric acid, tetrafluoroboric acid or hexafluoroantimonic acid, sodium salts or potassium salts of these protonic bodies, and most preferably protonic bodies of a perchloric acid, sodium perchlorate or potassium perchlorate.

As to the ratio of raw materials used, a peroxomonosulfate is used in a ratio by mol of, preferably, 0.1 to 10 mol, more preferably 1 to 6 mol, still more preferably 1.5 to 5 mol and still more preferably 2 to 4 mol to one mol of the compound represented by the formula (I).

The acid or its salt is used in a ratio by mol of, preferably, 0.5 to 20 mol, more preferably 1 to 10 mol, still more preferably 1.5 to 5 mol and still more preferably 2 to 4 mol to one mol of the compound represented by the formula (I).

As the solvent used in the reaction, for example, water, an amide type solvent (for example, N,N-dimethylformamide, N,N-dimethylacetamide and 1-methyl-2-pyrrolidone), sulfonic type solvent (for example, sulfolane), sulfoxide type solvent (for example, dimethylsulfoxide), ureide type solvent (for example, tetramethylurea), ether type solvent (for example, dioxane and cyclopentyl methyl ether), ketone type solvent (for example, acetone and cyclohexanone), hydrocarbon type solvent (for example, toluene, xylene and n-decane), halogen type solvent (for example, tetrachloroethane and chlorobenzene), alcohol type solvent (for example, methanol, ethanol, isopropyl alcohol, ethylene glycol, cyclohexanol and phenol), pyridine type solvent (for example, pyridine, γ-picoline and 2,6-lutidine), ester type solvent (for example, ethyl acetate and butyl acetate), carboxylic acid type solvent (for example, acetic acid and propionic acid) and nitrile type solvent (for example, acetonitrile) may be used either singly or in combinations. Among these compounds, water, an amide type solvent, sulfone type solvent, sulfoxide type solvent, ureide type solvent, halogen type solvent, alcohol type solvent, pyridine type solvent, ester type solvent, carboxylic acid type solvent and nitrile type solvent are preferable, water, an amide type solvent, sulfone type solvent, ureide type solvent, halogen type solvent, alcohol type solvent, ester type solvent and nitrile type solvent are more preferable, and water, sulfone type solvent, alcohol type solvent, ester type solvent and nitrile type solvent are still more preferable. Also, it is preferable to use a combination of water and other solvents.

The reaction temperature is −30 to 250° C., preferably −10 to 150° C., still more preferably −5 to 100° C., even more preferably 0 to 70° C. and even more preferably 10 to 50° C. It is also preferable to run the reaction at −5 to 20° C. at the start of the reaction and then at the temperature raised to 25 to 100° C. from the middle of the reaction.

According to the present invention, it is possible to provide a method in which an aminium salt and a diimmonium salt, which are near-infrared absorption dye compounds which are useful for image forming materials, infrared heat-sensitive recording materials, optical recording devices and optical film materials, can be produced readily, at low costs and in high yield.

The present invention will be described in more detail based on the following examples, but the present invention is not limited thereto.

EXAMPLES

Reference Example 1

Synthesis of Exemplified Compound (I-10)

According to the following scheme, Exemplified compound (I-10) was synthesized.

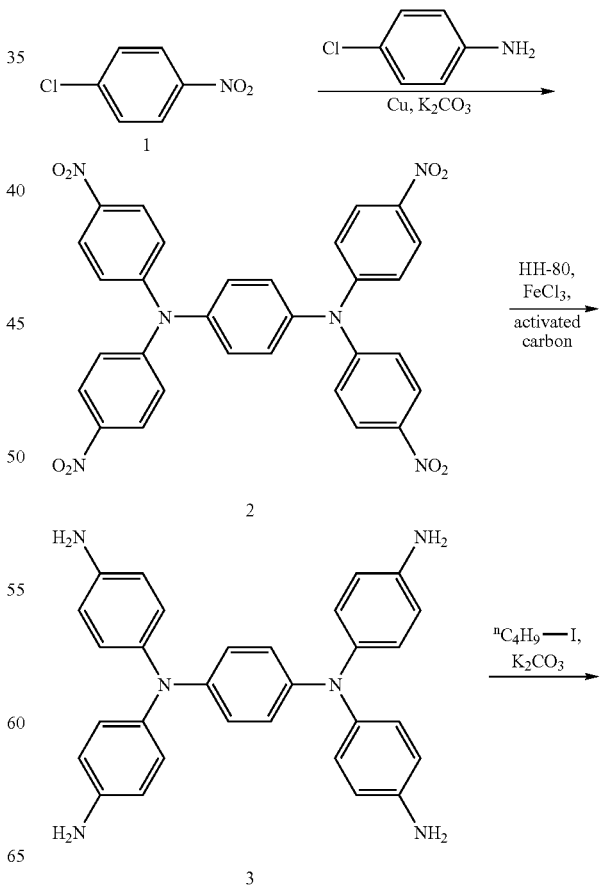

-continued

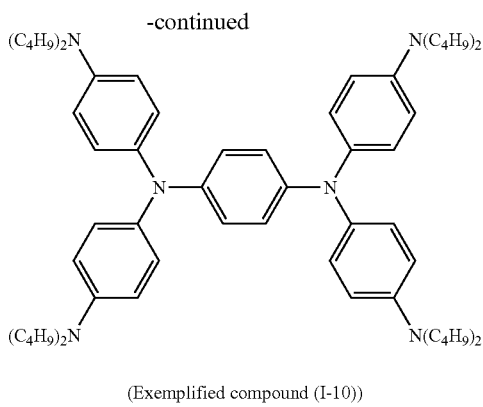

(Exemplified compound (I-10))

Synthesis of a Compound 2

A three-neck flask was charged with 56.5 g of p-phenylenediamine, 495 g of p-nitrochlorobenzene (1), 173.7 g of potassium carbonate, 750 ml of 1-methyl-2-pyrrolidone and 10 g of a copper powder and the mixture was stirred under heating and refluxing for 70 hours as it was. The reaction mixture was cooled to ambient temperature to obtain crystals, which were then washed with 1-methyl-2-pyrrolidone, washed with water and then dried by air, to obtain 297.3 g of the target compound 2 (yield: 96%). The mass-spectrum of this compound was measured, to find that M=592. Melting point: 300° C. or more.

Synthesis of a Compound 3

A three-neck flask was charged with 160 g of the compound 2, a solution containing 0.32 g of iron (III) chloride and 160 ml of isopropyl alcohol, 8.1 g of activated carbon and 1340 ml of 1-methyl-2-pyrrolidone and the mixture was heated until the internal temperature was raised to 100° C. with stirring. An aliquot of aqueous 80% solution dissolved hydrazine monohydrate (450 g) was added dropwise to the resulting mixture for one hour, stirred as it was under heating at an internal temperature of 100 to 110° C. with stirring continuously for 5 hours and then cooled to ambient temperature. The reaction mixture was subjected to filtration to remove activated carbon and the like. Then, 800 ml of methanol and 1200 ml of water were successively added dropwise to the reaction mixture to obtain crystals, which were then subjected to suction filtration and the residue was dried to obtain 125.2 g of the target compound 3 (yield: 98%). The mass-spectrum of this compound was measured, to find that M=472. Melting point: 300° C. or more.

Synthesis of (Exemplified Compound (I-10)

A three-neck flask was charged with 47.3 g of the compound 3, 165.9 g of potassium carbonate and 300 ml of 1-methyl-2-pyrrolidone and the mixture was stirred under heating, to which was added dropwise 220.8 g of 1-iodobutane for one hour at an internal temperature of 80° C. Heating and stirring were continued as it was at an internal temperature 82 to 93° C. for 3 hours and the mixture was then cooled to ambient temperature. The mixture was then extracted by adding 1000 ml of ethyl acetate and 1000 ml of water and the obtained ethyl acetate phase was washed with 1000 ml of water three times. The resulting product was concentrated by a rotary evaporator and the resulting residue was purified by silica gel column chromatography to obtain 88.5 g of the target exemplified compound (I-10) (yield: 96%). The mass-spectrum of this compound was measured, to find that M=920. Melting point: 104.5.

Example 1

Synthesis of the Exemplified Compound (II-3)

The exemplified compound (II-3) was synthesized according to the following scheme.

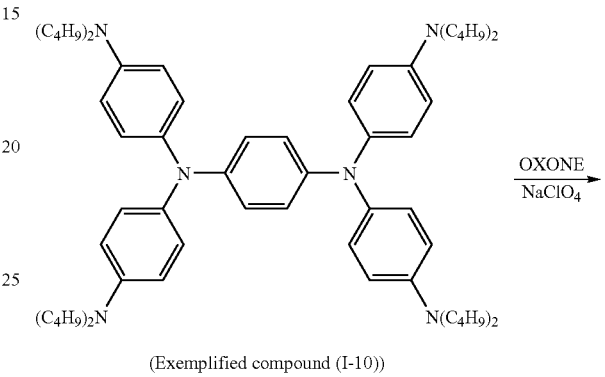

(Exemplified compound (I-10))

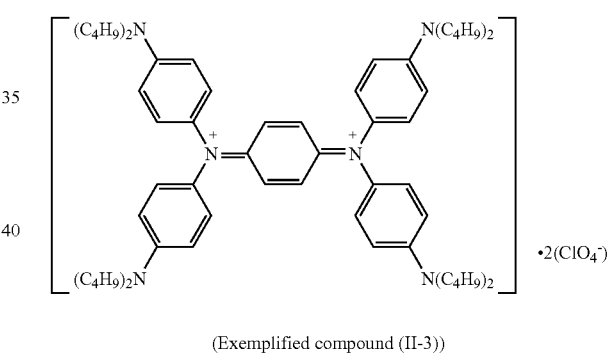

(Exemplified compound (II-3))

In a three-neck flask, 9.21 g of the exemplified (I-10) was dissolved in 120 ml of ethyl acetate, to which was then added 40 ml of acetonitrile and the mixture was stirred at ambient temperature. An aqueous solution prepared by dissolving 12.3 g of OXONE (trade name, commercially available from Sigma-Aldrich-Japan, having a composition of 2 $KHSO_5.KHSO_4.K_2SO_4$) manufactured by Du Pont and 2.44 g of sodium perchlorate in 40 ml of water was added dropwise to the mixture for 30 minutes, which was then stirred for 3 hours as it was. The resulting solution was fractionated and washed with a mixture solution of 60 ml of water and 10 ml of saturated brine three times. Then, the resulting mixture was concentrated by a rotary evaporator, ethyl acetate was added to the obtained residue and the obtained crystals were subjected to filtration and drying to obtain 10.4 g of the exemplified compound (II-3) (yield: 93%). The mass-spectrum of these crystals were measured in a unionized state to obtain the following results M/E=460. Also, DSC of these crystals was measured to obtain the following results: exothermic starting temperature: 186° C. and calorific value: 1,420 J/g.

Example 2

Synthesis of the Exemplified Compound (II-3)

The exemplified compound (II-3) was synthesized according to the following scheme.

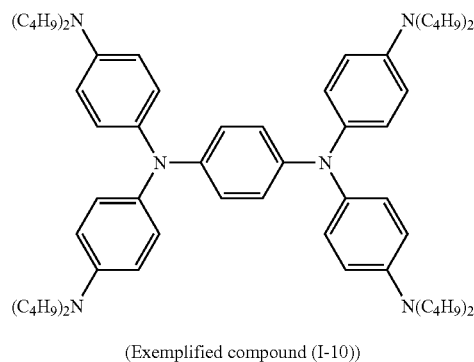

(Exemplified compound (I-10))

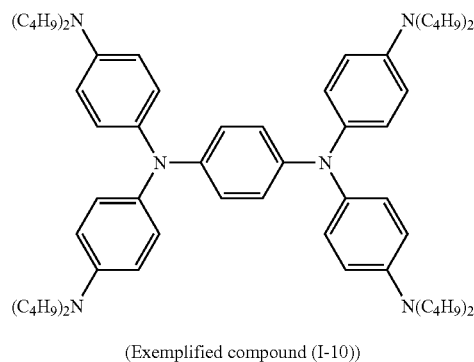

(Exemplified compound (II-3))

In a three-neck flask, 9.21 g of the exemplified (I-10) was dissolved in 120 ml of ethyl acetate, to which was then added 40 ml of acetonitrile and the mixture was stirred at ambient temperature. An aqueous solution prepared by dissolving 12.3 g of OXONE (trade name, commercially available from Sigma-Aldrich-Japan, having a composition of 2 $KHSO_5 \cdot KHSO_4 \cdot K_2SO_4$) manufactured by Du Pont and 2.77 g of potassium perchlorate in 40 ml of water was added dropwise to the mixture for 30 minutes, which was then stirred for 3 hours as it was. The resulting solution was fractionated and washed with a mixture solution of 60 ml of water and 10 ml of saturated brine three times. Then, the resulting mixture was concentrated by a rotary evaporator, ethyl acetate was added to the obtained residue and the obtained crystals were subjected to filtration and drying to obtain 10.6 g of the exemplified compound (II-3) (yield: 95%). The mass-spectrum of these crystals were measured in a unionized state to obtain the following results M/E=460.

Example 3

Synthesis of the Exemplified Compound (II-15)

The exemplified compound (II-15) was synthesized according to the following scheme.

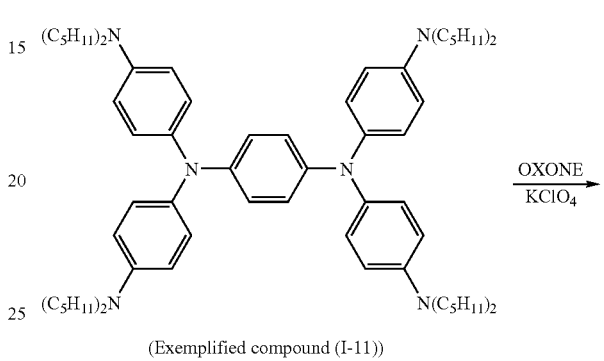

(Exemplified compound (I-11))

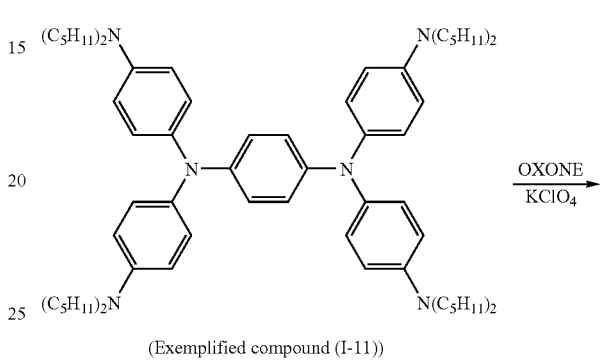

(Exemplified compound (II-15))

In a three-neck flask, 10.3 g of the exemplified (I-11) was dissolved in 120 ml of ethyl acetate, to which was then added 40 ml of acetonitrile and the mixture was stirred at ambient temperature. An aqueous solution prepared by dissolving 12.3 g of OXONE (trade name, commercially available from Sigma-Aldrich-Japan, having a composition of 2 $KHSO_5 \cdot KHSO_4 \cdot K_2SO_4$) manufactured by Du Pont and 2.77 g of potassium perchlorate in 40 ml of water was added dropwise to the mixture for 30 minutes, which was then stirred for 3 hours as it was. The resulting solution was fractionated and washed with a mixture solution of 60 ml of water and 10 ml of saturated brine three times. Then, the resulting mixture was concentrated by a rotary evaporator, ethyl acetate was added to the obtained residue and the obtained crystals were subjected to filtration and drying to obtain 11.2 g of the exemplified compound (II-15) (yield: 91%). The mass-spectrum of these crystals were measured in a unionized state to obtain the following results MIE=516.

Example 4

Synthesis of the Exemplified Compound (II-7)

The exemplified compound (II-7) was synthesized according to the following scheme.

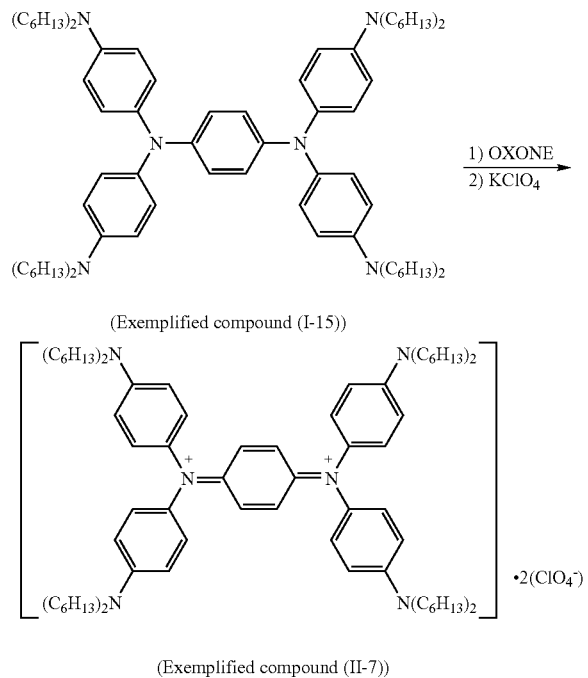

In a three-neck flask, 11.46 g of the exemplified (I-15) was dissolved in 150 ml of ethyl acetate, to which was then added 50 ml of acetonitrile and the mixture was stirred at ambient temperature. An aqueous solution prepared by dissolving 12.3 g of OXONE (trade name, commercially available from Sigma-Aldrich-Japan, having a composition of 2 $KHSO_5 \cdot KHSO_4 \cdot K_2SO_4$) manufactured by Du Pont in 40 ml of water was added dropwise to the mixture for 30 minutes, which was then stirred for 3 hours as it was. An aqueous solution dissolving 2.77 g of potassium perchlorate in 40 ml of water was added, and the mixture was stirred for 1 hour as it was. The resulting solution was fractionated and washed with a mixture solution of 60 ml of water and 10 ml of saturated brine three times. Then, the resulting mixture was concentrated by a rotary evaporator, ethyl acetate was added to the obtained residue and the obtained crystals were subjected to filtration and drying to obtain 12.10 g of the exemplified compound (II-7) (yield: 90%). The mass-spectrum of these crystals were measured in a unionized state to obtain the following results M/E=572.

Example 5

Synthesis of the Exemplified Compound II-33

The exemplified compound (II-33) was synthesized according to the following scheme.

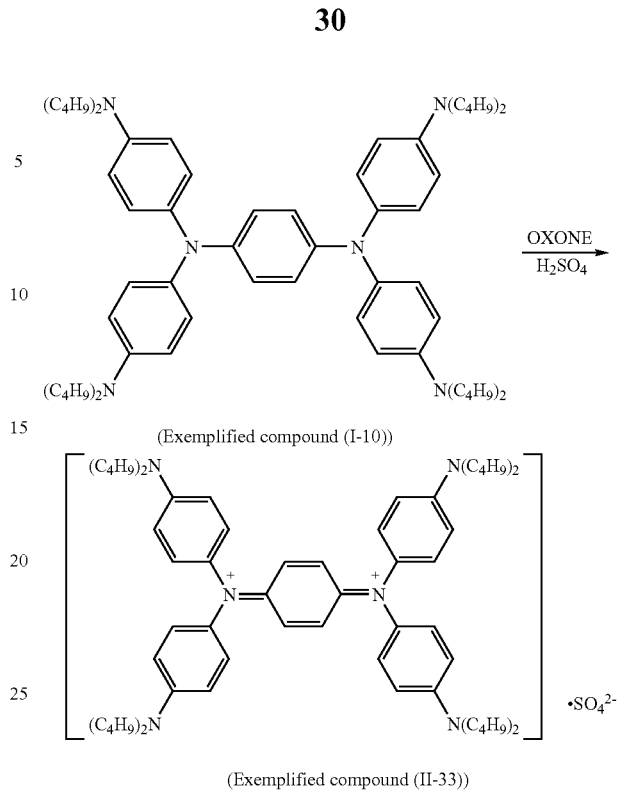

In a three-neck flask, 9.21 g of the exemplified (I-10) was dissolved in 120 ml of ethyl acetate, to which was then added 40 ml of acetonitrile and the mixture was stirred at ambient temperature. An aqueous solution prepared by dissolving 12.3 g of OXONE (trade name, commercially available from Sigma-Aldrich-Japan, having a composition of 2 $KHSO_5 \cdot KHSO_4 \cdot K_2SO_4$) manufactured by Du Pont and 1.96 g of sulfuric acid in 40 ml of water was added dropwise to the mixture for 30 minutes, which was then stirred for 3 hours as it was. The resulting solution was fractionated and washed with a mixture solution of 60 ml of water and 10 ml of saturated brine three times. Then, the resulting mixture was concentrated by a rotary evaporator, ethyl acetate was added to the obtained residue and the obtained crystals were subjected to filtration and drying to obtain 9.4 g of the exemplified compound (II-33) (yield: 92%). The mass-spectrum of these crystals were measured in a unionized state to obtain the following results M/E=460.

Example 6

Synthesis of the Exemplified Compound (II-3)

In a three-neck flask, 9.21 g of the exemplified compound (I-10) was dissolved in 120 ml of acetonitrile, and the mixture was stirred at ambient temperature. After addition of 12.3 g of OXONE (trade name, commercially available from Sigma-Aldrich-Japan, having a composition of $2KHSO_5 \cdot KHSO_4 \cdot K_2SO_4$) manufactured by Du Pont to the mixture, and the mixture was then stirred for 3 hours as it was. To the filtrate which was obtained by filtrating the resulting mixture to remove crystals, 3.9 g of sodium perchlorate was added, and the mixture was stirred for 1 hour as it was, to which 40 ml of ethyl acetate and 100 ml of water were added, and was stirred. The thus-obtained crystals were subjected to filtration and drying to obtain 11.0 g of the exemplified compound (II-3) (yield: 98%). The mass spectrum of these crystals were measured in a unionized state to obtain the following results M/E=460.

As described above, according to the present invention, diimonium compounds were obtained at high yields of 90% or higher, by using peroxomonosulfuric acid or its salt as an oxidizing agent. Particularly, as to the production of divalent diimonium compound as described in the aforementioned example, a high yield over 90% production of the diimonium compound was possible to carry out by using the peroxomonosulfuric acid or its salt, although it is described in Example 4 of JP-A-2003-55643 that diimonium compound was produced in a low yield (as low as 60%) by the method using peroxodisulfate.

Having described our invention as related to the present embodiments, it is our intention that the invention not be limited by any of the details of the description, unless otherwise specified, but rather be construed broadly within its spirit and scope as set out in the accompanying claims.

What we claim is:

1. A method of producing a near-infrared absorbing dye compound, comprising a process of reacting a compound represented by formula (I) with peroxomonosulfuric acid or its salt:

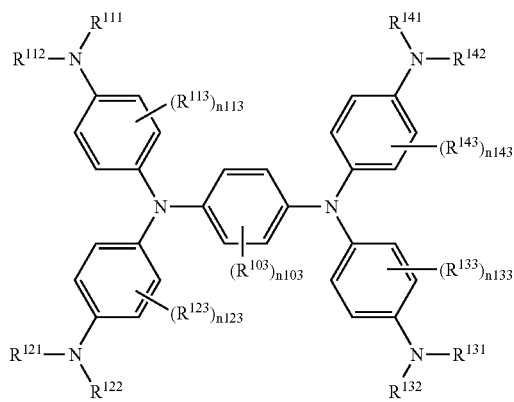

Formula (I)

wherein $R^{111}$, $R^{112}$, $R^{121}$, $R^{122}$, $R^{131}$, $R^{132}$, $R^{141}$ and $R^{142}$ each independently represent a hydrogen atom, an aliphatic group or an aromatic group; $R^{103}$, $R^{113}$, $R^{123}$, $R^{133}$ and $R^{143}$ each independently represent a substituent; and $n_{103}$, $n_{113}$, $n_{123}$, $n_{133}$ and $n_{143}$ each independently denote an integer from 0 to 4.

2. The production method according to claim 1, wherein the salt of peroxomonosulfuric acid is potassium peroxohydrogen monosulfate.

3. The production method according to claim 1, wherein the near-infrared absorbing dye compound is a diimonium salt represented by formula (II):

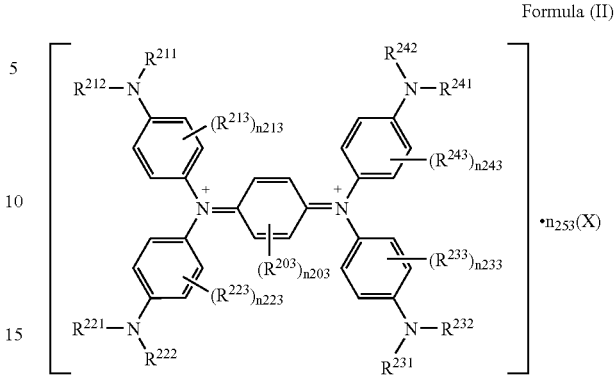

Formula (II)

wherein $R^{211}$, $R^{212}$, $R^{221}$, $R^{222}$, $R^{231}$, $R^{232}$, $R^{241}$ and $R^{242}$ each independently represent a hydrogen atom, an aliphatic group or an aromatic group; $R^{203}$, $R^{213}$, $R^{223}$, $R^{233}$ and $R^{243}$ each independently represent a substituent; $n_{203}$, $n_{213}$, $n_{223}$, $n_{233}$ and $n_{243}$ each independently denote an integer from 0 to 4; X represents a monovalent or divalent anion; and $n_{253}$ represents a number of 1 or 2, provided that the product of the valence number of X and $n_{253}$ is 2.

4. The production method according to claim 3, wherein X is a divalent anion.

5. The production method according to claim 1, wherein an acid or its salt coexists in the process.

6. The production method according to claim 5, wherein the acid or its salt is perchloric acid or a perchlorate.

7. The production method according to claim 1, wherein $R^{111}$, $R^{112}$, $R^{121}$, $R^{122}$, $R^{131}$, $R^{132}$, $R^{141}$ and $R^{142}$ each are an alkyl group having 2 to 6 carbon atoms, which are the same each other.

8. The production method according to claim 1, wherein $R^{103}$, $R^{113}$, $R^{123}$, $R^{133}$ and $R^{143}$ each are an alkyl group.

9. The production method according to claim 1, wherein $R^{113}$, $R^{123}$, $R^{133}$ and $R^{143}$ each are an alkyl group, which are the same each other.

10. The production method according to claim 1, wherein $n_{103}$, $n_{113}$, $n_{123}$, $n_{133}$ and $n_{143}$ each are zero.

11. The production method according to claim 3, wherein $R^{211}$, $R^{212}$, $R^{221}$, $R^{222}$, $R^{231}$, $R^{232}$, $R^{241}$ and $R^{242}$ each are an alkyl group having 2 to 6 carbon atoms, which are the same each other.

12. The production method according to claim 3, wherein $R^{203}$, $R^{213}$, $R^{223}$, $R^{233}$ and $R^{243}$ each are an alkyl group.

13. The production method according to claim 3, wherein $R^{213}$, $R^{223}$, $R^{233}$ and $R^{243}$ each are an alkyl group, which are the same each other.

14. The production method according to claim 3, wherein $n_{203}$, $n_{213}$, $n_{223}$, $n_{233}$ and $n_{243}$ each are zero.

15. The production method according to claim 3, wherein X is a perchloric acid ion, in the case that X is a monovalent anion, or a carbonate ion, sulfate ion, oxalate ion, succinate ion, malonate ion, chromate ion, bichromate ion, or teteraborate ion, in the case a divalent anion.

16. The production method according to claim 3, wherein peroxomonosulfuric acid or its salt is potassium peroxohydrogen monosulfate, or a composition mixed with potassium peroxohydrogen monosulfate and a sulfate thereof.

* * * * *